United States Patent
Parker et al.

(10) Patent No.: US 9,933,326 B2
(45) Date of Patent: Apr. 3, 2018

(54) SYSTEM AND METHOD FOR DETECTING MICROSCOPIC LEAKS

(71) Applicant: REDLINE DETECTION, LLC, Orange, CA (US)

(72) Inventors: Zachary Parker, Newport Coast, CA (US); Mark C. Hawkins, Fullerton, CA (US)

(73) Assignee: REDLINE DETECTION, LLC, Orange, CA (US)

( * ) Notice: Subject to any disclaimer, the term of this patent is extended or adjusted under 35 U.S.C. 154(b) by 0 days.

(21) Appl. No.: 15/215,706

(22) Filed: Jul. 21, 2016

(65) Prior Publication Data
US 2017/0023433 A1    Jan. 26, 2017

Related U.S. Application Data

(60) Provisional application No. 62/195,613, filed on Jul. 22, 2015.

(51) Int. Cl.
*G01M 3/20* (2006.01)
*G01M 3/22* (2006.01)
(Continued)

(52) U.S. Cl.
CPC .............. *G01M 3/20* (2013.01); *G01M 3/226* (2013.01); *B05B 1/24* (2013.01); *F24F 6/08* (2013.01);
(Continued)

(58) Field of Classification Search
CPC ..................................................... G01M 3/20
(Continued)

(56) References Cited

U.S. PATENT DOCUMENTS 1,506,418 A    8/1924  Evensta et al.
1,510,212 A    9/1924  Du Bois
(Continued)

FOREIGN PATENT DOCUMENTS

DE    4411928    1/1995
JP    S56110032  9/1981
(Continued)

OTHER PUBLICATIONS

Intake Pressure Testers for the Turbocharged Mitsubishi 3000GT/ Dodge Stealth; http://www.stealth316.com/2-pressuretester.htm, Retrieved via Internet Archive. Dated Feb. 16, 2007.
(Continued)

*Primary Examiner* — Manish S Shah
*Assistant Examiner* — Timothy Graves
(74) *Attorney, Agent, or Firm* — Stetina Brunda Garred & Brucker

(57) ABSTRACT

A universal leak detection method for detecting both small and large leaks. The method includes the steps of: injecting smoke and a detectable gas into a fluid system to pressurize the fluid system, the smoke and detectable gas both being capable of passing through a large leak in the fluid system, and the visual smoke particles being inhibited from passing through a small leak in the fluid system and the detectable gas being capable of passing through a small leak in the fluid system; and detecting a leak by detecting at least one of the smoke and the detectable gas, wherein detection of smoke is indicative of the fluid system having a large leak and detection of detectable gas without smoke.

13 Claims, 4 Drawing Sheets

(51) Int. Cl.
- B05B 1/24 (2006.01)
- G01M 3/04 (2006.01)
- F41H 9/06 (2006.01)
- G01N 27/26 (2006.01)
- G01M 3/28 (2006.01)
- F24F 6/08 (2006.01)

(52) U.S. Cl.
CPC .............. *F41H 9/06* (2013.01); *G01M 3/04* (2013.01); *G01M 3/042* (2013.01); *G01M 3/28* (2013.01); *G01N 27/26* (2013.01)

(58) Field of Classification Search
USPC ........................................................ 73/40.7
See application file for complete search history.

(56) References Cited

U.S. PATENT DOCUMENTS

| | | | |
|---|---|---|---|
| 1,710,439 A | 9/1926 | Taylor | |
| 2,192,155 A | 4/1937 | Schuldt | |
| 2,299,116 A | 5/1941 | Svirsky | |
| 2,273,984 A | 2/1942 | Osborn | |
| 2,753,876 A | 3/1955 | Kurt | |
| 2,764,243 A | 9/1956 | Page | |
| 3,024,200 A | 3/1962 | Smith | |
| 3,075,535 A | 1/1963 | Lasting | |
| 3,234,357 A | 2/1966 | Seuthe | |
| 3,431,945 A | 3/1969 | Robillard | |
| 3,431,946 A | 3/1969 | Sawyer | |
| 3,583,239 A | 6/1971 | Paine | |
| 3,837,214 A | 9/1974 | Guest | |
| 3,870,085 A | 3/1975 | Schneider | |
| 4,352,515 A | 10/1982 | Schumacher | |
| 4,354,515 A | 10/1982 | Sutherland | |
| 4,373,381 A | 2/1983 | Kulp et al. | |
| 4,373,767 A | 2/1983 | Cairns | |
| 4,460,019 A | 7/1984 | Condon | |
| 4,524,607 A | 6/1985 | Pelletier et al. | |
| 4,550,751 A | 11/1985 | Shimamura | |
| 4,608,858 A | 9/1986 | McKinnon | |
| 4,750,525 A | 6/1988 | Vaughn | |
| 4,764,660 A | 8/1988 | Swiatosz | |
| 4,818,843 A | 4/1989 | Swiatosz | |
| 4,905,931 A | 3/1990 | Covey | |
| 5,022,435 A | 6/1991 | Jaw-Shiunn | |
| 5,328,152 A | 6/1994 | Castle | |
| 5,353,842 A | 10/1994 | Lundman | |
| 5,425,266 A | 1/1995 | Fournier | |
| 5,390,738 A | 2/1995 | Eslinger et al. | |
| 5,501,115 A | 3/1996 | Kamiyama et al. | |
| 5,647,054 A | 7/1997 | Jones | |
| 5,735,955 A | 4/1998 | Monaghan et al. | |
| 5,771,937 A | 6/1998 | Collins | |
| 5,859,363 A | 1/1999 | Gouge | |
| 5,922,944 A | 7/1999 | Pieroni et al. | |
| 6,018,615 A * | 1/2000 | Loblick | F41H 9/06 261/142 |
| 6,131,441 A | 10/2000 | Berube et al. | |
| 6,142,009 A | 11/2000 | Loblick | |
| 6,175,987 B1 | 1/2001 | Harvey | |
| 6,267,001 B1 | 7/2001 | Duncan | |
| 6,314,795 B1 | 11/2001 | Ingham | |
| 6,336,482 B1 | 1/2002 | Cunkle et al. | |
| 6,348,869 B1 | 2/2002 | Ashworth | |
| 6,361,752 B1 | 3/2002 | Demarest et al. | |
| 6,389,613 B1 | 5/2002 | Comas | |
| 6,392,227 B1 | 5/2002 | Banyard et al. | |
| 6,439,031 B1 | 8/2002 | Pieroni et al. | |
| 6,439,931 B1 | 8/2002 | Pieroni et al. | |
| 6,502,603 B2 | 1/2003 | Lane, Jr. | |
| 6,526,808 B1 * | 3/2003 | Pieroni | G01M 3/2807 73/40.7 |
| 6,651,486 B1 | 11/2003 | Johnson | |
| 6,653,005 B1 * | 11/2003 | Muradov | B01J 8/009 429/410 |
| 6,899,138 B2 | 5/2005 | Lundman | |
| 6,907,771 B2 | 6/2005 | Finlay et al. | |
| 7,305,176 B1 * | 12/2007 | Pieroni | F24F 11/0086 239/135 |
| 8,689,611 B2 * | 4/2014 | Enquist | G01M 3/22 73/40.7 |
| 2001/0035046 A1 | 11/2001 | Williams | |
| 2002/0152801 A1 | 10/2002 | Burke et al. | |
| 2003/0047881 A1 | 2/2003 | Worm et al. | |
| 2007/0079649 A1 | 12/2007 | Nauseda et al. | |
| 2007/0297774 A1 | 12/2007 | Pieroni | |
| 2009/0315326 A1 | 12/2009 | Pieroni | |
| 2010/0095746 A1 | 4/2010 | Lund | |
| 2011/0290006 A1 | 12/2011 | Perkins et al. | |
| 2012/0197250 A1 | 8/2012 | Ward | |
| 2013/0247651 A1 | 9/2013 | Grange | |
| 2013/0319540 A1 | 12/2013 | Hegner | |
| 2014/0083168 A1 | 3/2014 | Parker et al. | |
| 2014/0151242 A1 | 6/2014 | Thompson et al. | |
| 2014/0251831 A1 * | 9/2014 | Ley | G01M 3/042 205/780.5 |

FOREIGN PATENT DOCUMENTS

| | | |
|---|---|---|
| JP | 59126223 | 7/1984 |
| JP | 59138935 | 8/1984 |
| JP | S9138935 A | 8/1984 |
| JP | 2003004581 | 1/2003 |

OTHER PUBLICATIONS

DSM Boost Leaks/Turbo intake Pressure Tester; http://www.mirage-performance.com/EclipseGSX/BoostLeaks/index.html, Retrieved via Internet Archive. Dated Feb. 8, 2007.

Patent Cooperation Treaty International Search Report; PCT/US2013060732; dated Feb. 11, 2014; 5 pages.

European Patent Office Extended Search Report; 13841836.1-1557/2901066; 3 pages.

Thomas, Shane, Patent Cooperation Treaty PCT International Search Report and Written Opinion, dated Oct. 18, 2016, 18 pages.

Aerolab "Smoke Generator", Oct. 2, 2014 (Retrieved from Internet: Sep. 27, 2016) URL: http:/www.aerolab.com/products/smoke-generator/; p. 2, paragraph 2.

* cited by examiner

SYSTEM AND METHOD FOR DETECTING MICROSCOPIC LEAKS

CROSS-REFERENCE TO RELATED APPLICATIONS

This application claims the benefit of U.S. Provisional Application No. 62/195,613, entitled System and Method for Detecting Microscopic Leaks, filed Jul. 22, 2015, the contents of which are expressly incorporated herein by reference.

STATEMENT RE: FEDERALLY SPONSORED RESEARCH/DEVELOPMENT

Not Applicable

BACKGROUND

1. Technical Field

The present disclosure relates generally to leak detection within a fluid system, and more specifically to leak detection using a visual vapor and a detectable gas generated with the visual vapor, with the detectable gas being used specifically for detecting small leaks within the fluid system.

2. Description of the Related Art

Most vehicles include fluid systems which may be critical to the overall operation of the vehicle. Indeed, a vehicle's air braking system, air suspension system, intake system, exhaust system, cooling system, air conditioning system and sealed components may be fluid systems. If a fluid system on a vehicle begins leaking, the system may not function properly. Furthermore, if heavy duty trucks exceed a Department of Transportation specified maximum air brake system leakdown rate, the vehicle may be deemed unsafe to operate and removed from service. Accordingly, detecting leaks in fluid systems is critical to the overall operability of the vehicle.

Currently, there are several methods for detecting leaks in a fluid system. One particular method is to pressurize the fluid system with air and to listen for leaks. A common deficiency with this method is that the leaks may not be discernable without specialized listening devices, which are typically rendered useless in loud environments, such as a typical vehicle repair facility. Furthermore, not all leaks create a harmonic vibration that can be detected with listening devices.

Another known method for detecting leaks includes injecting a visual vapor or smoke into the system and look for the smoke leaking from the system. This particular method tends to work well for larger leaks. However, in the case of smaller leaks, the vaporized oil particles in the visible smoke may be too large to pass through a microscopic leak orifice. Accordingly, the technician may not be provided with a visual cue associated with a large leak because only the air is passing through the orifice while the oil particles are left behind.

Another method used to detect leaks is to inject a dye into the system and to look for a dye stain around the leak orifice. As with the smoke example above, the dye molecules may be held back in cases of microscopic leaks, rendering this method ineffective. Furthermore, in larger systems, such as an air induction system or an air brake system on a heavy duty tractor with multiple trailers connected, it would be very difficult to properly coat all internal surfaces of the fluid system to perform an effective test. Also some OEM manufacturers forbid the use of dyes and other contaminants into their vehicles, as some believe that the dye can coat or harm critical sensors. Furthermore, the dye oil may include solvents which manufacturers of diesel particulate filters and other catalytic devices strongly suggest that their products are not exposed to out of fear of an exothermal event which may harm the microthin catalytic coating of palladium, platinum, etc.

Accordingly, there is a need in the art for an easy to use, universal leak detection system and related method, which may be used to detect and locate large, medium and microscopic leaks with a single test in large, medium and small fluid systems. Various aspects of the present disclosure address this particular need, as will be discussed in more detail below.

BRIEF SUMMARY

There is provided a system and related method which employs a multi-tiered approach to detecting and locating large, medium and microscopic leaks. More specifically, a visual vapor is used to identify large leaks, while a gas detector or sniffer is used to detect small leaks by searching for a leaking gas. The system may also allow for leak detection by smelling a distinct scent associated with the leaking gas.

According to one embodiment, there is provided a method of testing a fluid system for leaks. The method includes the steps of: heating a smoke agent to generate visual vapor and a gaseous byproduct; injecting the visual vapor and gaseous byproduct into a fluid system to pressurize the fluid system; and detecting leakage of the gaseous byproduct from the fluid system to indicate the presence of a leak in the fluid system.

The smoke agent used in the heating step may be white mineral oil or polyalkylene glycol oil. The gaseous byproduct generated during the heating step may be hydrogen.

The fluid system into which the visual vapor and gaseous byproduct are injected may be a fluid system on a motor vehicle. The fluid system on the vehicle may be an air brake system.

The injecting of the visual vapor and the gaseous byproduct into the fluid system may occur in a single step.

The detecting step may include the use of a gas detector. The gas detector may include a low sensitivity mode and a high sensitivity mode, wherein the detecting step may include switching the sensitivity mode between the low sensitivity mode and the high sensitivity mode.

According to another aspect of the present disclosure, there is provided a universal leak detection method for detecting both small and large leaks. The method includes the steps of: injecting smoke and a detectable gas into a fluid system to pressurize the fluid system, the smoke and detectable gas both being capable of passing through a large leak in the fluid system, and the smoke being inhibited from passing through a small leak in the fluid system and the detectable gas being capable of passing through a small leak in the fluid system; and detecting a leak by detecting at least one of the smoke and the detectable gas, wherein detection of smoke is indicative of the fluid system having a large leak and detection of detectable gas without smoke.

The method may further comprise the step of detecting the detectable gas. The detecting step may include the use of a gas detector.

According to yet another embodiment of the present disclosure, there is provided a leak detection system comprising a smoke generator capable of heating a smoke agent to generate visual vapor and a gaseous byproduct and injecting the visual vapor and gaseous byproduct into a fluid system. The system further includes a gas detector configured to detect the gaseous byproduct generated by the smoke generator.

The gas detector may be capable of detecting hydrogen.

The smoke generator may be capable of heating white mineral oil or polyalkylene glycol oil to generate the visual vapor and hydrogen.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

Figure 1:
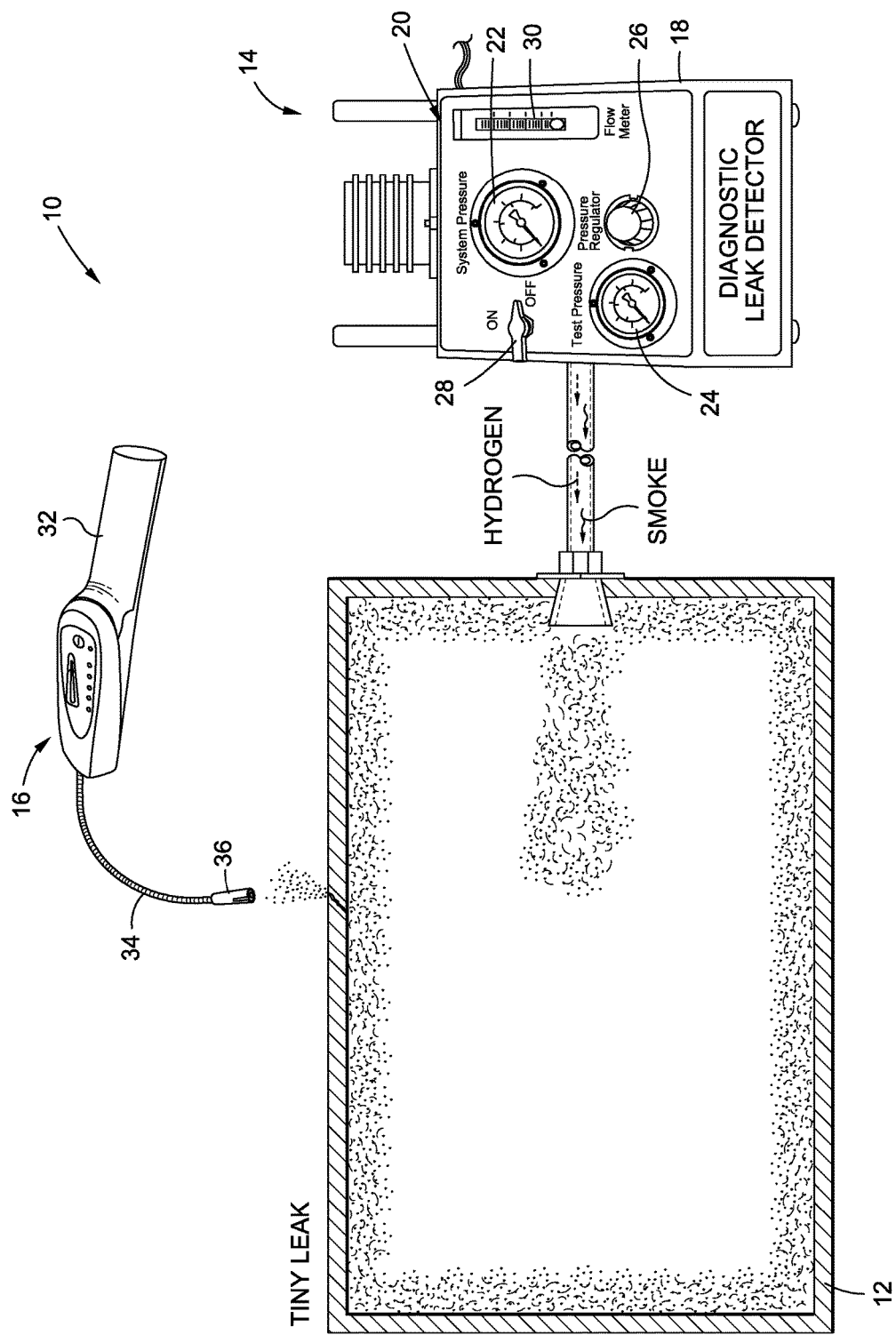
FIG. 1 is a schematic view of a leak detection system being used to detect a small fluid leak.
Figure 2:
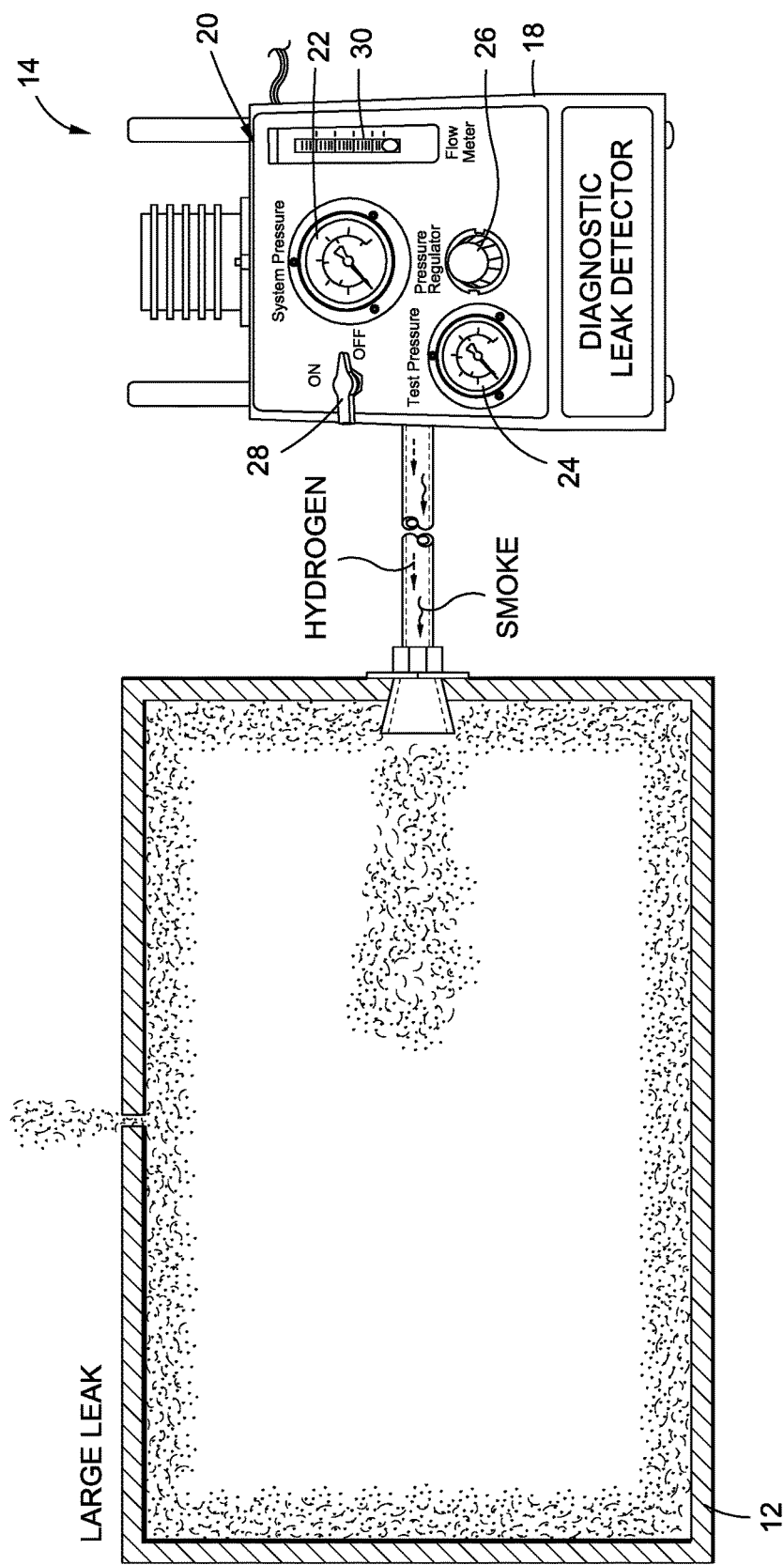
FIG. 2 is a schematic view of a leak detection system being used to detect a large fluid leak.
Figure 3:
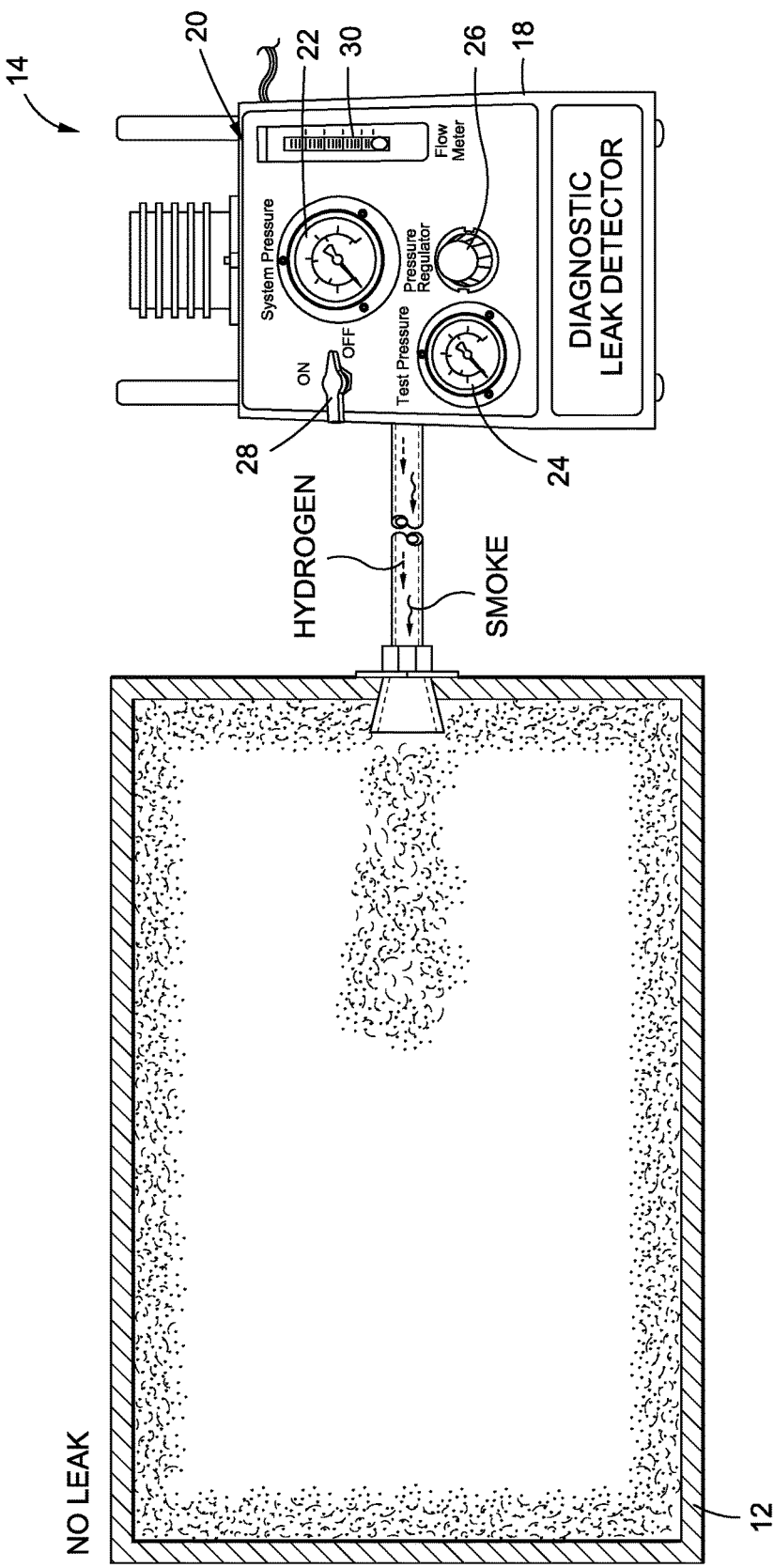
FIG. 3 is a schematic view of a fluid system having no fluid leaks.
Figure 4:
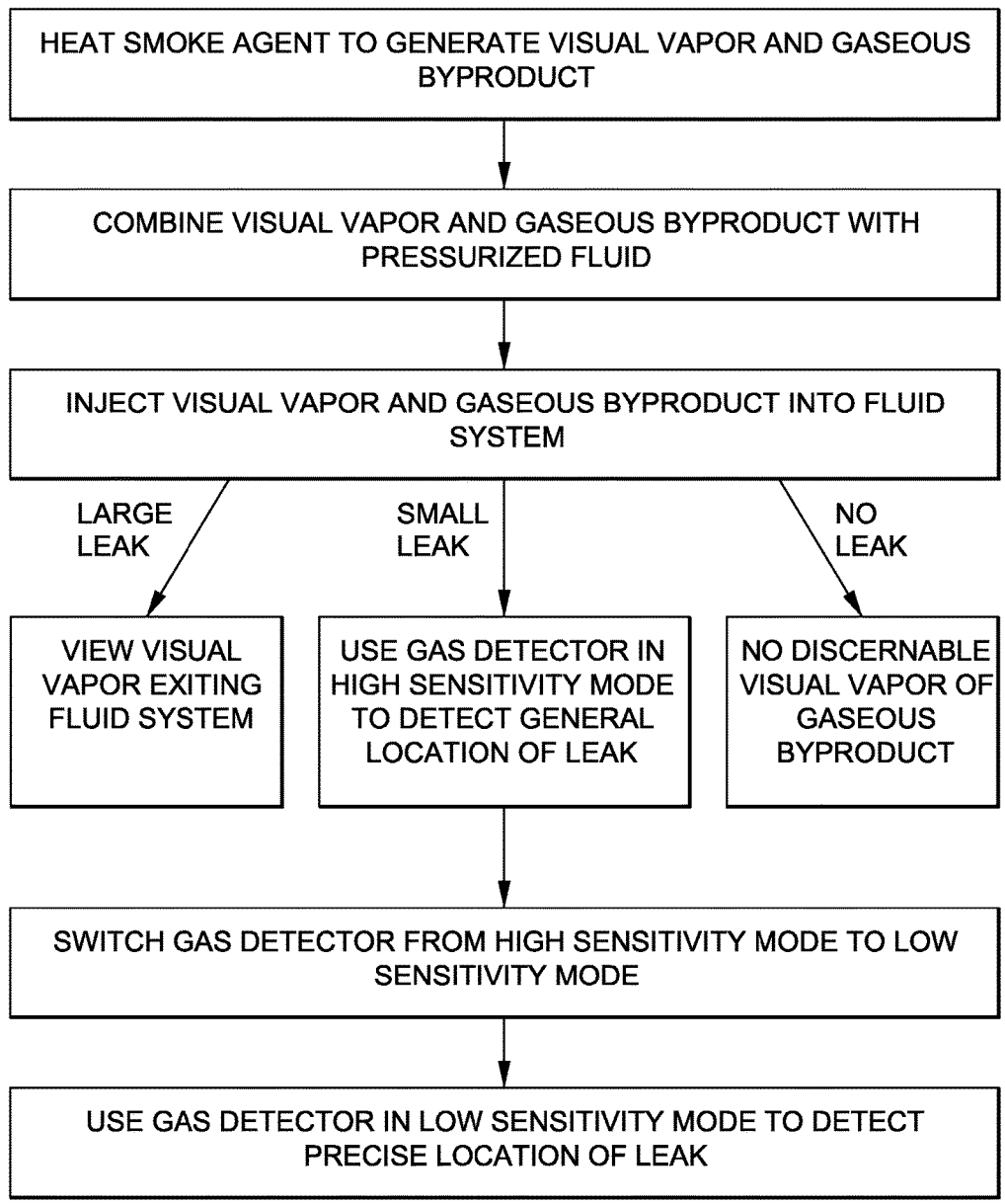
FIG. 4 is a flow chart of an exemplary method of detecting both small and large leaks in a fluid system.

The detailed description set forth below in connection with the appended drawings is intended as a description of certain embodiments of a leak detection system and related method and is not intended to represent the only forms that may be developed or utilized. The description sets forth the various structure and/or functions in connection with the illustrated embodiments, but it is to be understood, however, that the same or equivalent structure and/or functions may be accomplished by different embodiments that are also intended to be encompassed within the scope of the present disclosure. It is further understood that the use of relational terms such as first and second, and the like are used solely to distinguish one entity from another without necessarily requiring or implying any actual such relationship or order between such entities.

According to various aspects of the present disclosure, there is provided a universal system 10 and related method which may be used to detect both large and small leaks in a fluid system 12. In this regard, the same equipment and procedure may be used for detecting leaks that are large and small in size. As noted above, many conventional leak detection systems are not universal in nature, and thus, are more suitable for detecting either one of large leaks or small leaks. Consequently, the system and methodology disclosed herein provides several advantages over conventional leak detection systems.

The leak detection system 10 generally includes a smoke generator 14 and a gas detector 16. The smoke generator 14 includes a housing 18 having a fluid reservoir for holding a smoke producing fluid. According to one embodiment, the smoke producing fluid is a fluid which when heated to a certain temperature will produce a dense, non-toxic smoke. Suitable fluids include non-toxic petroleum based oils, such as a white mineral oil, polyalkylene glycol oil, or other smoke-producing fluids known by those skilled in the art. While the term "smoke" generally refers to the visual vapor and particulate that is a byproduct of incomplete combustion, the term "smoke" as used herein includes any visible gas, vapor, and/or aerosol (particulate suspended in a gas) or any combination thereof. Furthermore, the term "vaporize" means to transform a fluid into a smoke.

The smoke generator 14 further includes a heating element for vaporizing the smoke producing fluid into smoke. According to one embodiment, the heating element is a coil of resistive wire which generates heat when an electrical current is conducted therethrough. The coil may be in communication with the smoke producing fluid via a fluid transfer device or wick that delivers the smoke producing fluid from the reservoir to the coil. One suitable wire for the heating element is a 20 gauge alloy-52 wire (52% nickel, 48% iron) available from Strategic Aerospace Materials in Hicksville, N.Y. Other suitable wire or resistive heating materials known in the art may be used without departing from the spirit and scope of the present disclosure.

A unique aspect of the present disclosure is that the smoke generator 14 is configured to not only generate smoke, but the smoke generator 14 also produces a gaseous byproduct, which is particularly useful when detecting small leaks, as will be discussed in more detail below. The gaseous byproduct may be generated by the smoke generator 14 when the smoke is generated. In other words, the gaseous byproduct may be a result of the heating of the smoke generating fluid. The gaseous byproduct may be hydrogen, argon, nitrogen, carbon dioxide, or any other gases known or used in the art for leak detection. According to one implementation, the gaseous byproduct has a distinct odor, which may be useful when testing for leaks. In this regard, if the user smells the odor when testing, it is likely that a leak is present within the fluid system 12.

In one embodiment, the production of the gaseous byproduct by the smoke generator 14 is precisely mapped or corresponds to the gas detector 16 used during testing. In this regard, various parameters (e.g., temperature, pressure, etc.) may be set when operating the smoke machine 14 to produce a gaseous byproduct having certain characteristics which may facilitate detection during testing. The operating pressure of the system may range from 0.4 PSI to 325 PSI. Testing pressures are adjusted for the system being inspected as required. For automotive fuel vapor recovery systems, the test pressure may be just under 0.5 PSI; to test a turbo system, the test pressure may be 10-20 PSI; to test an air brake system on a heavy duty truck, the test pressure may be 80-120 PSI; to test an air conditioning system the test pressure should be 30-325 PSI. The smoke agent oil may be heated to temperatures ranging from 220° F. to 410° F.

In order to convey the smoke and gaseous byproduct produced by the smoke generator into a fluid system to check for leaks, a source of pressurized gas, such as compressed air, may be supplied to the smoke before the smoke is delivered via a delivery conduit. A pressure regulator may be in communication with the source of pressurized gas to reduce the incoming gas pressure to the desired pressure depending on the type of fluid system that is to be leak checked. Examples of the types of fluid systems that may be leak checked include, but are not limited to, air brake systems, air suspension systems, intake and exhaust systems, cooling systems, and sealed components for heavy duty trucks/equipment, intake and exhaust systems, cooling systems, and sealed components for automobiles and medium duty trucks, as well as fluid systems in residential and commercial buildings, including heating, ventilation, and air conditioning systems and ducts, and compressed air lines in industrial building and plumbing applications.

The smoke generator 14 additionally includes a controller for controlling the generation of smoke by the smoke generator 14. In this regard, the controller may be capable of turning on and off the power to the heating element based on temperature and/or cycle-time criteria. In this regard, the controller may be programmed to energize the heating element when the temperature of the heating element is below a specified temperature and to de-energize the heating element when the temperature of the heating element exceeds a specified temperature. Alternatively, in a more complex control scheme, the controller may be programmed to initially energize the heating element for a specified period of time. At the end of the initial time period, the controller de-energizes the heating element. The controller then evaluates the temperature of the heating element and if the temperature of the heating element is below a specified value, the controller again energizes the heating element for another specified period of time (which may be the same or a different length of time as the initial time period). The cycle continues until the heating element reaches the prescribed operating temperature such that the controller de-energizes the heating element. Then, the heating element is left de-energized for a specified period of time. After the specified period of time has expired, the controller evaluates the temperature of the heating element and if the heating element is above a specified temperature, the heating element remains de-energized. If the heating element is below the specified temperature, the controller energizes the heating element. This cycle continues for as long as the smoke generator 14 is being used to produce smoke.

The smoke generator 14 may include a user interface 20 to allow the user to control certain functions of the smoke generator 14, as well as to provide the user with certain information during operation of the smoke generator 14. For instance, the user interface 20 may include a system pressure gauge 22 depicting the pressure of the system being tested, a test pressure gauge 24 depicting the desired testing pressure, a pressure regulator 26 to allow a user to set the testing pressure, a flow controller 28 to control the fluid flow from the smoke generator 14 to the fluid system 12, and a flow meter 30 depicting the actual flow from the smoke generator 14 to the fluid system 12. According to one embodiment, the user interface 20 is analog (i.e., non-digital), while in other embodiments, the user interface 20 may be digital. The user interface 20 may be in communication with the controller to autonomously implement various functions or performance parameters (e.g., pressure settings, temperature settings, fluid flow settings), based on selections made by the user. For instance, particularly in the case of a digital user interface, the user interface 20 may be configured to allow the user to select a specific fluid system 12 that is to be tested, and the controller may implement particular performance parameters that are pre-programmed to correspond to the selected fluid system.

According to one embodiment, the smoke generator 14 is configured to perform a leak down (e.g., decay) test and provide a pass/fail light as per the Department of Transportation regulations for the vehicle under test. This feature provides a significant improvement over conventional leak down testing, wherein a technician is required to look at a dashboard gauge to try and determine the amount of decay within 60 seconds.

Although the foregoing describes certain features related to the smoke generator 14, additional details may be found in U.S. Pat. No. 7,305,176, entitled Method and Device for Detecting Leaks Using Smoke, the contents of which are expressly incorporated herein by reference. Furthermore, an exemplary smoke generator is the POWERSMOKE PRO™, available from Redline Detection LLC in Orange, Calif.

In addition to the smoke generator 14, the leak detection system 10 further includes a gas detector 16 configured to detect the gaseous byproduct generated by the smoke generator 14. The gas detector 16 is preferably sized and configured to be hand-holdable, and may be carried by a user to search for leaking gas. One embodiment of the gas detector 16 includes a main body 32 and a flexible sniffer arm 34 extending from the main body 32 and having a sniffer probe 36 disposed at the end of the sniffer arm 34 opposite the main body 32. The flexibility of the sniffer arm 34 allows the sniffer probe 36 to access hard to reach locations.

The sniffer probe 36 may be capable of detecting the gaseous byproduct generated by the smoke generator 14. In this regard, the sniffer probe 36 may be capable of detecting hydrogen gas, or other gases known or used in the art for detecting leaks.

The sniffer probe 36 is in communication with a central processing unit, preferably housed in the main body 32. When the sniffer probe 36 detects a specified concentration of a prescribed gas, the sniffer probe 36 communicates a signal to the central processing unit. The central processing unit will then generate an alert signal for alerting the user that the prescribed gas has been detected. The alert signal may be an audible signal transmitted from the main body 32, and/or a visual signal emitted from the main body 32. In this regard, the main body 32 may include one or more LEDs 38 or a display screen for displaying a visual signal. The amplitude or intensity of the alert signal may vary in accordance with the amount or concentration of the prescribed gas that is detected.

According to certain embodiments, the gas detector 16 may be capable of modifying the sensitivity of the sniffer probe 36 between at least two different sensitivity modes, including a low sensitivity mode, and a high sensitivity mode. In the low sensitivity mode, the gas detector 16 will require detection of a higher concentration or level of the prescribed gas before generating an alert signal, relative to the high sensitivity mode. Conversely, the gas detector 16 will require detection of a lower concentration or level of the prescribed gas before generating an alert signal, relative to the low sensitivity mode. The gas detector 16 may include a switch, button, or other activation mechanism on the main body 32 for allowing the user to selectively transition operation of the gas detector 16 between the low sensitivity mode and the high sensitivity mode.

An exemplary gas detector 16 is the C-16 PortaSens II Gas Detector by Analytical Technology, Inc., located in Collegeville, Pa., although other gas detectors known in the art may be used without departing from the spirit and scope of the present disclosure.

With the basic structure of the system 10 described above, the following discussion focuses on a method of using the system 10. The method includes using the smoke generator 14 to heat a smoke agent to generate a visual vapor and a gaseous byproduct. In particular, the heating element in the smoke generator may be actuated to heat the smoke producing fluid to vaporize the fluid. According to one embodiment, the vaporization of the smoke producing fluid also results in generation of the gaseous byproduct. In this regard, various aspects of the present disclosure are directed to a method wherein the visual vapor and the gaseous byproduct are both generated, substantially simultaneously, by the smoke generator 14. However, it is understood that the visual vapor and the gaseous byproduct may be independently generated by different sources without departing from the spirit and scope of the present disclosure.

The visual vapor and the gaseous byproduct are combined with a pressurized fluid, and are injected into the fluid system 12 to pressurize the fluid system 12. According to one embodiment, the injecting of the visual vapor and the gaseous byproduct into the fluid system 12 occurs in a single step, and substantially simultaneously.

Once the visual vapor and the gaseous byproduct has been injected into the fluid system 12, the user searches for leaks in the fluid system 12. In the case of a large leak, the visual vapor will escape from the fluid system 12, and may produce an easily visible indication of a leak, as well as the location of the leak. However, in the case of a small leak, the visual vapor may not be able to escape from the fluid system 12, and thus, small leaks may not be as readily discernable. However, although the visual vapor may not escape through the small leak, the gaseous byproduct can escape, and thus, the user may detect the small leaks by using the gas detector 14 to detect leakage of the gaseous byproduct. When the gas detector 14 is used, the user may initially place the gas detector 14 in the high sensitivity mode such that the gas detector 14 will provide an alert when even the smallest amount of the gaseous byproduct is detected. As such, the user will be able to determine a general location of the leak. Subsequently, the user may transition the gas detector 14 from the high sensitivity mode to the low sensitivity mode to more specifically determine the location of the leak. In this regard, by switching to the low sensitivity mode, the gas detector 14 will require detection of a higher concentration or level of the gaseous byproduct before generating an alert signal, and thus, the gas detector 14 will need to be in much closer proximity to the leak before generating an alert. For instance, if there is a leak around a fluid-fitting in the fluid system, using the gas detector 14 in the low sensitivity mode may allow the user to determine from which side of the fitting the gas is leaking.

The above described system and related method is a significant improvement on conventional leak detecting techniques. In this regard, the method of using the system is universal in the sense that it may be used to detect both large and small leaks.

The particulars shown herein are by way of example only for purposes of illustrative discussion, and are not presented in the cause of providing what is believed to be most useful and readily understood description of the principles and conceptual aspects of the various embodiments of the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. A method of testing a fluid system for leaks, the method comprising the steps of:
    injecting a visual vapor and a detectable gas into the fluid system to pressurize the fluid system;
    using a gas detector in a high sensitivity mode to detect leakage of the detectable gas from the fluid system to initially identify a general location of the leakage of the detectable gas, the gas detector providing an alert in response to detection of a first concentration of the detectable gas by the gas detector when the gas detector is in the high sensitivity mode;
    transitioning the gas detector from the high sensitivity mode to a low sensitivity mode after the general location has been identified, the gas detector providing an alert in response to detection of a second concentration of the detectable gas which is higher than the first concentration; and
    using the gas detector in the low sensitivity mode to detect leakage of the detectable gas within the general location to more specifically identify a precise location of the leakage of the detectable gas.

2. The method recited in claim 1, wherein the detectable gas injected into the fluid system is hydrogen.

3. The method recited in claim 1, wherein the fluid system into which the visual vapor and detectable gas are injected is a fluid system on a motor vehicle.

4. The method recited in claim 3, wherein the fluid system on the motor vehicle is an air brake system.

5. The method recited in claim 1, wherein the injecting of the visual vapor and the detectable gas into the fluid system occurs in a single step.

6. The method recited in claim 1, further comprising the step of combining the visual vapor and the detectable gas with a pressurized fluid.

7. A universal leak detection method for detecting both a small leak and a large leak, the method comprising the steps of:
    injecting smoke and a detectable gas simultaneously into a fluid system to pressurize the fluid system, the smoke and detectable gas both being capable of passing through the large leak in the fluid system, and the smoke being inhibited from passing through the small leak in the fluid system and the detectable gas being capable of passing through the small leak in the fluid system;
    detecting a leak by detecting at least one of the smoke and the detectable gas, wherein detection of smoke is indicative of the fluid system having a large leak and detection of detectable gas without smoke, wherein detection of the detectable gas includes:
        using a gas detector in a high sensitivity mode to identify a general location from which leakage of the detectable gas occurs, the gas detector providing an alert in response to detection of a first concentration of the detectable gas by the gas detector when the gas detector is in the high sensitivity mode; and
        using the gas detector in the low sensitivity mode after use of the gas detector in the high sensitivity mode to detect leakage of the detectable gas within the general location.

8. The method recited in claim 7, further comprising the step of detecting the detectable gas.

9. The method recited in claim 7, wherein the detectable gas is hydrogen.

10. The method recited in claim 7, wherein the fluid system into which the smoke and detectable gas are injected is a fluid system on an automobile.

11. The method recited in claim 10, wherein the fluid system on the automobile is an air brake system.

12. The method recited in claim 7, wherein the injecting of the smoke and the detectable gas into the fluid system occurs in a single step.

13. The method recited in claim 7, wherein the smoke and detectable gas are injected under pressure.

* * * * *